US010722126B2

(12) United States Patent
Chang et al.

(10) Patent No.: US 10,722,126 B2
(45) Date of Patent: Jul. 28, 2020

(54) HEART RATE DETECTION METHOD AND DEVICE THEREOF

(71) Applicant: NATIONAL YUNLIN UNIVERSITY OF SCIENCE AND TECHNOLOGY, Yunlin County (TW)

(72) Inventors: Chuan-Yu Chang, Yunlin County (TW); Hsiang-Chi Liu, Taipei (TW); Matthew Huei-Ming Ma, Yunlin (TW)

(73) Assignee: NATIONAL YUNLIN UNIVERSITY OF SCIENCE AND TECHNOLOGY, Yunlin County (TW)

( * ) Notice: Subject to any disclaimer, the term of this patent is extended or adjusted under 35 U.S.C. 154(b) by 122 days.

(21) Appl. No.: 16/202,110

(22) Filed: Nov. 28, 2018

(65) Prior Publication Data

US 2020/0163560 A1     May 28, 2020

(51) Int. Cl.
| | | |
|---|---|---|
| *A61B 5/024* | (2006.01) |
| *G06T 7/73* | (2017.01) |
| *G06K 9/00* | (2006.01) |
| *G06T 7/00* | (2017.01) |
| *A61B 5/00* | (2006.01) |
| *A61B 5/11* | (2006.01) |

(52) U.S. Cl.
CPC ........ *A61B 5/02416* (2013.01); *A61B 5/1102* (2013.01); *A61B 5/1128* (2013.01); *A61B 5/7257* (2013.01); *G06K 9/00281* (2013.01); *G06T 7/0016* (2013.01); *G06T 7/74* (2017.01); *A61B 2576/02* (2013.01); *G06T 2207/20056* (2013.01); *G06T 2207/30041* (2013.01); *G06T 2207/30201* (2013.01)

(58) Field of Classification Search
CPC . A61B 5/02416; A61B 5/7257; A61B 5/1128; A61B 5/1102; A61B 2576/02; G06T 7/0016; G06T 7/74; G06T 2207/30201; G06T 2207/30041; G06T 2207/20056; G06K 9/00281
See application file for complete search history.

(56) References Cited

PUBLICATIONS

Guha Balakrishnan et al., "Detecting Pulse from Head Motions in Video", 2013 IEEE Conference on Computer Vision and Pattern Recognition, dated on Jun. 23-28, 2013, pp. 3430-3437, United States.

*Primary Examiner* — Christopher Wait
(74) *Attorney, Agent, or Firm* — CKC & Partners Co., LLC

(57) ABSTRACT

A heart rate detection method includes a facial image data acquiring step, a feature points recognizing step, an effective displacement signal generating step and a heart rate determining step. The feature points recognizing step is for recognizing a plurality of feature points, wherein a number range of the feature points is from three to twenty, and the feature points include a center point between two medial canthi, a point of a pronasale and a point of a subnasale of the face. The effective displacement signal generating step is for calculating an original displacement signal, wherein the original displacement signal is converted to an effective displacement signal. The heart rate determining step is for transforming the effective displacement signals of each of the feature points to an effective spectrum, wherein a heart rate is determined from one of the effective spectrums corresponding to the feature points, respectively.

10 Claims, 7 Drawing Sheets

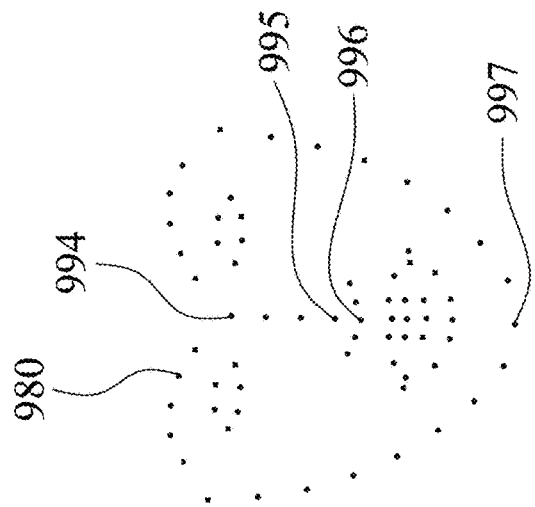
Fig. 6
Fig. 4
Fig. 5
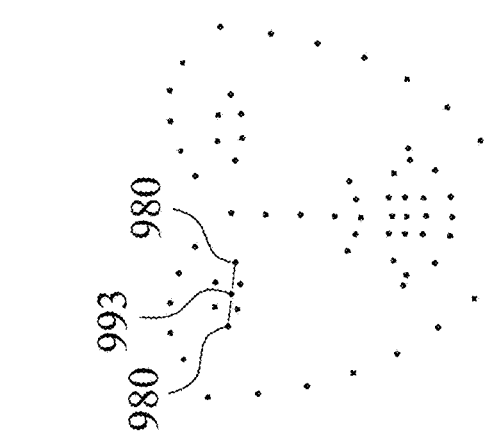
Fig. 3

HEART RATE DETECTION METHOD AND DEVICE THEREOF

BACKGROUND

Technical Field

The present disclosure relates to a heart rate detection method and a device thereof. More particularly, the present disclosure relates to a non-contact heart rate detection method from a face and a device thereof.

Description of Related Art

Cardiovascular diseases (CVD) are the main causes of illness and even death. Heart is the most important organ of the body, and it reflects the vital signs of human and also affects the physiological functions of the body. Heart rate is the most directly part of monitoring physiological information. Continuous monitoring of heart rate can provide a statistical analysis of long-term trends for physicians.

With the vigorous development of information technology, the heart rate detection methods are diversely. The heart rate detection methods can be roughly divided into two categories: contact and non-contact. The contact heart rate detection method is required to paste electrodes on the subject's skin to process, wherein the famous devices of the contact heart rate detection method include electrocardiograph (ECG) and handheld ECG devices. However, the contact heart rate detection devices need to touch the body of the subjects, which may cause discomfort or irritation of the body. For special groups, such as infants, elders, and patients with wound, it may cause a great burden on the body.

In order to improve the aforementioned situations, the non-contact heart rate devices have been recently proposed, such as Doppler radar, life detectors and cameras. Among them, using the cameras to measure the heart rate is more suitable in daily life. The video-based heart rate detection methods could be roughly divided into three categories: thermal imaging, photoplethysmography (PPG), and head oscillations. In a conventional video-based heart rate detection method, a principle of optical flow to detect the pulse is applied. However, the heart rate detection method is suffering from the influences under the complex environment such as illumination changes, non-frontal face, and so on.

Given the above, the conventional heart rate detection methods and the devices thereof are usually affected by the illumination changes, the non-frontal face, the facial expressions and so on, so that an effective heart rate detection method and a device thereof has become one of the important subjects in the market.

SUMMARY

According to one aspect of the present disclosure, a heart rate detection method includes a facial image data acquiring step, a feature points recognizing step, an effective displacement signal generating step and a heart rate determining step. The facial image data acquiring step is for acquiring a plurality of frames of facial image data of a face. The feature points recognizing step is for recognizing a plurality of feature points, which are pre-determined, of the face from the plurality of frames of facial image data, wherein a number range of the feature points is from three to twenty, and the feature points include a center point between two medial canthi, a point of a pronasale and a point of a subnasale of the face. The effective displacement signal generating step is for calculating an original displacement signal of each frame time of each of the feature points from the plurality of frames of facial image data, wherein the original displacement signal is established based on an original horizontal displacement and an original vertical displacement, and converted to an effective displacement signal. The heart rate determining step is for transforming the effective displacement signals of each of the feature points to an effective spectrum, wherein a heart rate is determined from one of the effective spectrums corresponding to the feature points, respectively.

According to another aspect of the present disclosure, a heart rate detection device includes a photographing unit, a heart rate calculation unit and an output unit. The photographing unit is configured to provide a plurality of frames of facial image data of a face. The heart rate calculation unit is communicatively connected to the photographing unit, wherein the heart rate calculation unit is configured to recognize a plurality of feature points, which are pre-determined, of the face from the plurality of frames of facial image data, a number range of the feature points is from three to twenty, the feature points include a center point between two medial canthi, a point of a pronasale and a point of a subnasale of the face, an effective displacement signal of each frame time of each of the feature points is calculated from the plurality of frames of facial image data, the effective displacement signals of each of the feature points are transformed to an effective spectrum, and a heart rate is determined from one of the effective spectrums corresponding to the feature points, respectively. The output unit is communicatively connected to the heart rate calculation unit, wherein the heart rate is outputted to the output unit from the heart rate calculation unit.

BRIEF DESCRIPTION OF THE DRAWINGS

The present disclosure can be more fully understood by reading the following detailed description of the embodiment, with reference made to the accompanying drawings as follows:

FIG. 3 is a schematic view of a feature point according to the 1st embodiment.

FIG. 4 is a schematic view of another feature point according to the 1st embodiment.

FIG. 5 is a schematic view of still another feature point according to the 1st embodiment.

FIG. 6 is a schematic view of yet another feature points according to the 1st embodiment.

DETAILED DESCRIPTION

The embodiment will be described with the drawings. For clarity, some practical details will be described below. However, it should be noted that the present disclosure should not be limited by the practical details, that is, in some embodiment, the practical details is unnecessary. In addition, for simplifying the drawings, some conventional structures and elements will be simply illustrated, and repeated elements may be represented by the same labels.

Figure 1:
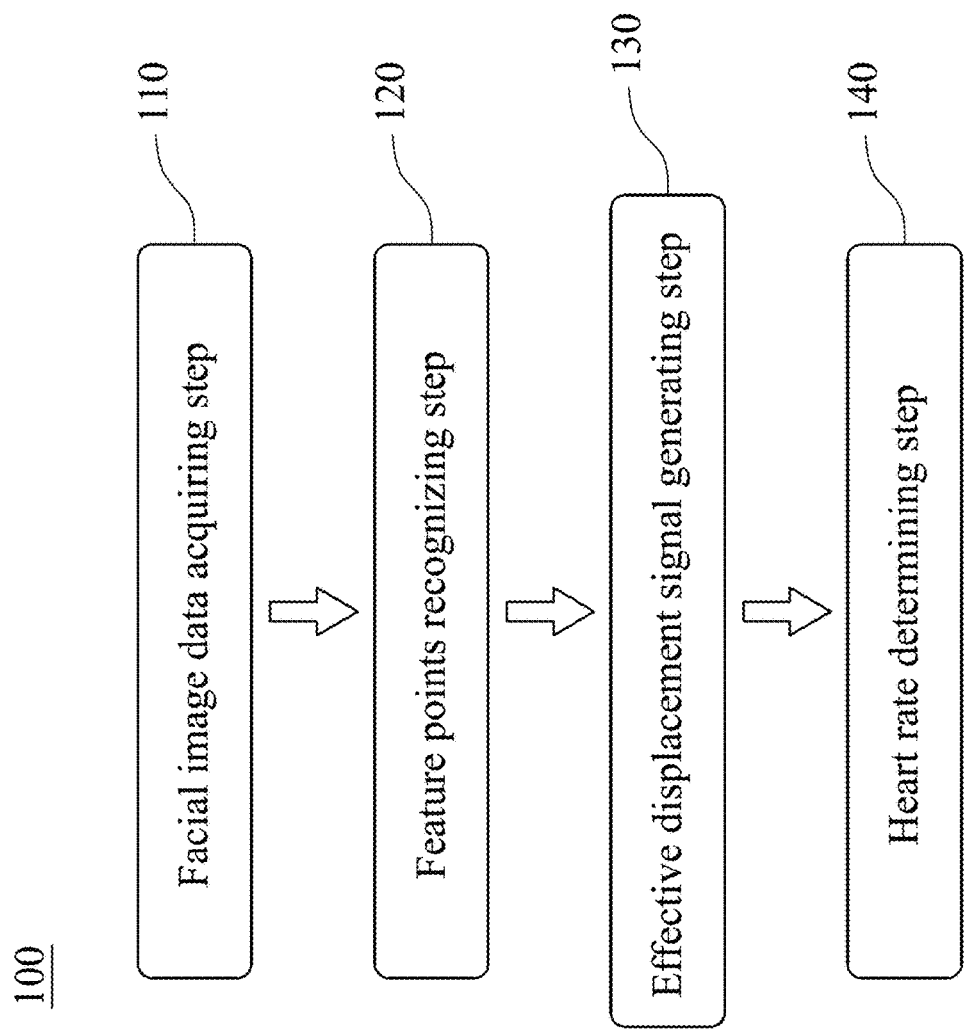
FIG. 1 is a flow chart of a heart rate detection method according to the 1st embodiment of the present disclosure.

FIG. 1 is a flow chart of a heart rate detection method 100 according to the 1st embodiment of the present disclosure. In FIG. 1, the heart rate detection method 100 includes a facial image data acquiring step 110, a feature points recognizing step 120, an effective displacement signal generating step 130 and a heart rate determining step 140.

Figure 2:
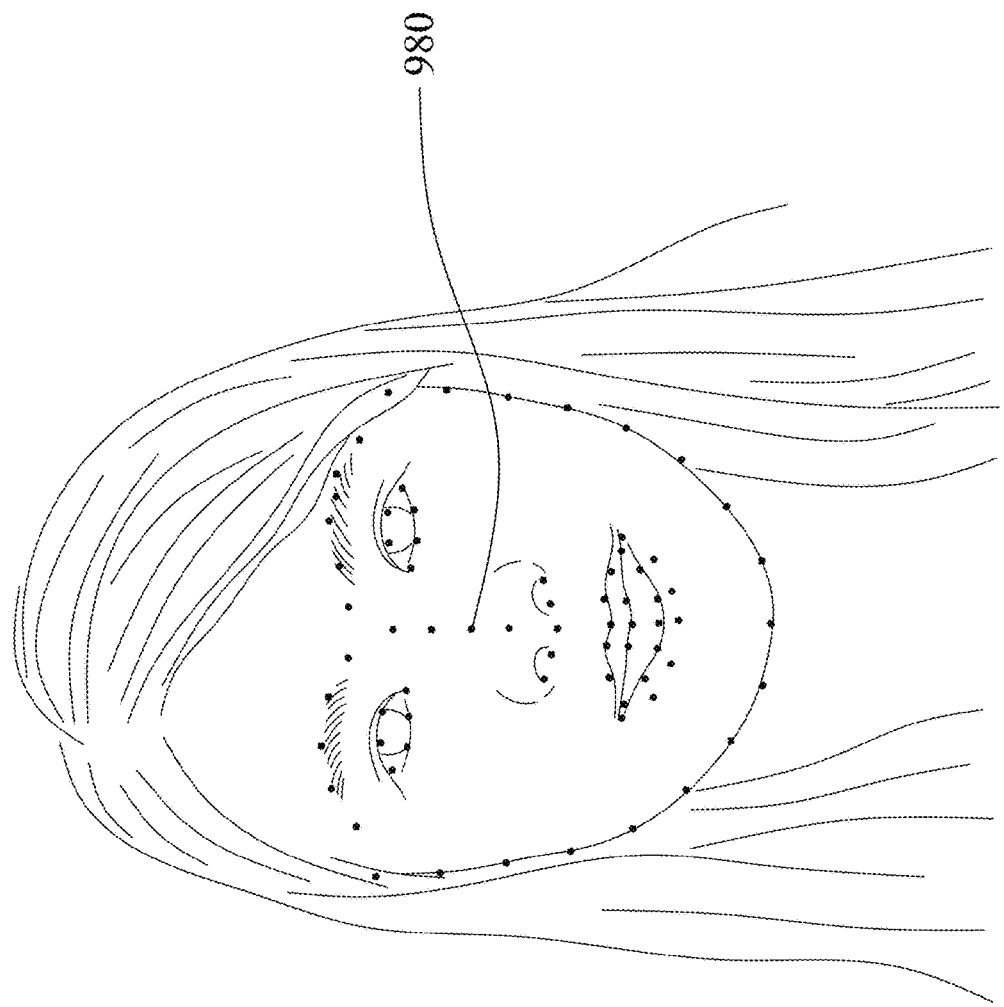
FIG. 2 is a schematic view of landmark points according to the 1st embodiment.

FIG. 2 is a schematic view of a plurality of landmark points 980 according to the 1st embodiment. FIG. 3 is a schematic view of a feature point 991 according to the 1st embodiment. FIG. 4 is a schematic view of a feature point 992 according to the 1st embodiment. FIG. 5 is a schematic view of a feature point 993 according to the 1st embodiment. FIG. 6 is a schematic view of feature points 994, 995, 996, 997 according to the 1st embodiment. In FIG. 2 to FIG. 6, the facial image data acquiring step 110 is for acquiring a plurality of frames of facial image data of a face 900. The feature points recognizing step 120 is for recognizing the plurality of feature points, which are pre-determined, of the face 900 from the plurality of frames of facial image data, wherein a number range of the feature points is from three to twenty. That is, at least the feature points 991, 995, 996 of the face 900 are included, wherein the feature point 991 is a center point between two medial canthi of the face 900, the feature point 995 is a point of a pronasale of the face 900, and the feature point 996 is a point of a subnasale of the face 900.

Figure 7:
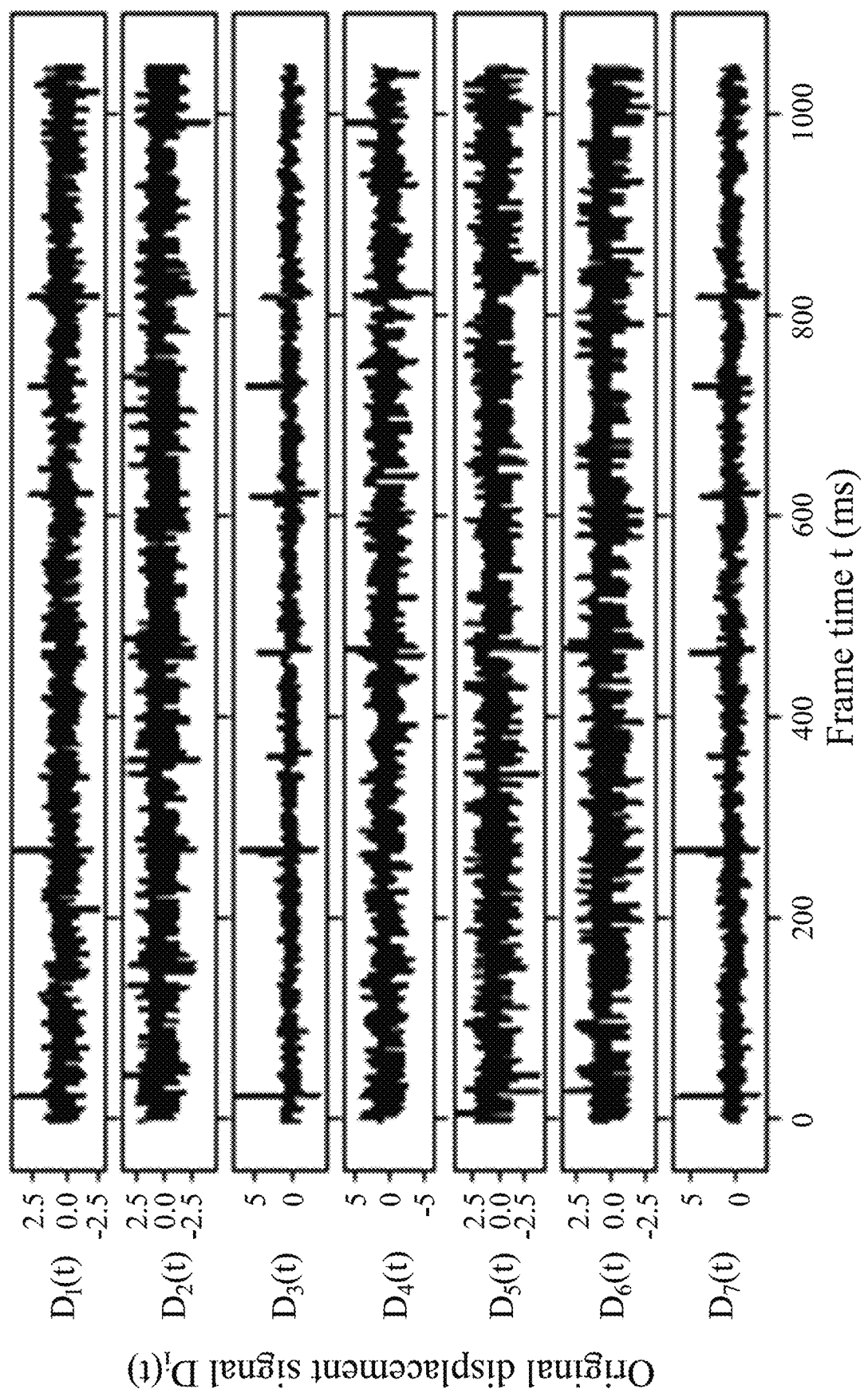
FIG. 7 is a schematic view of original displacement signals according to the1st embodiment.
Figure 8:
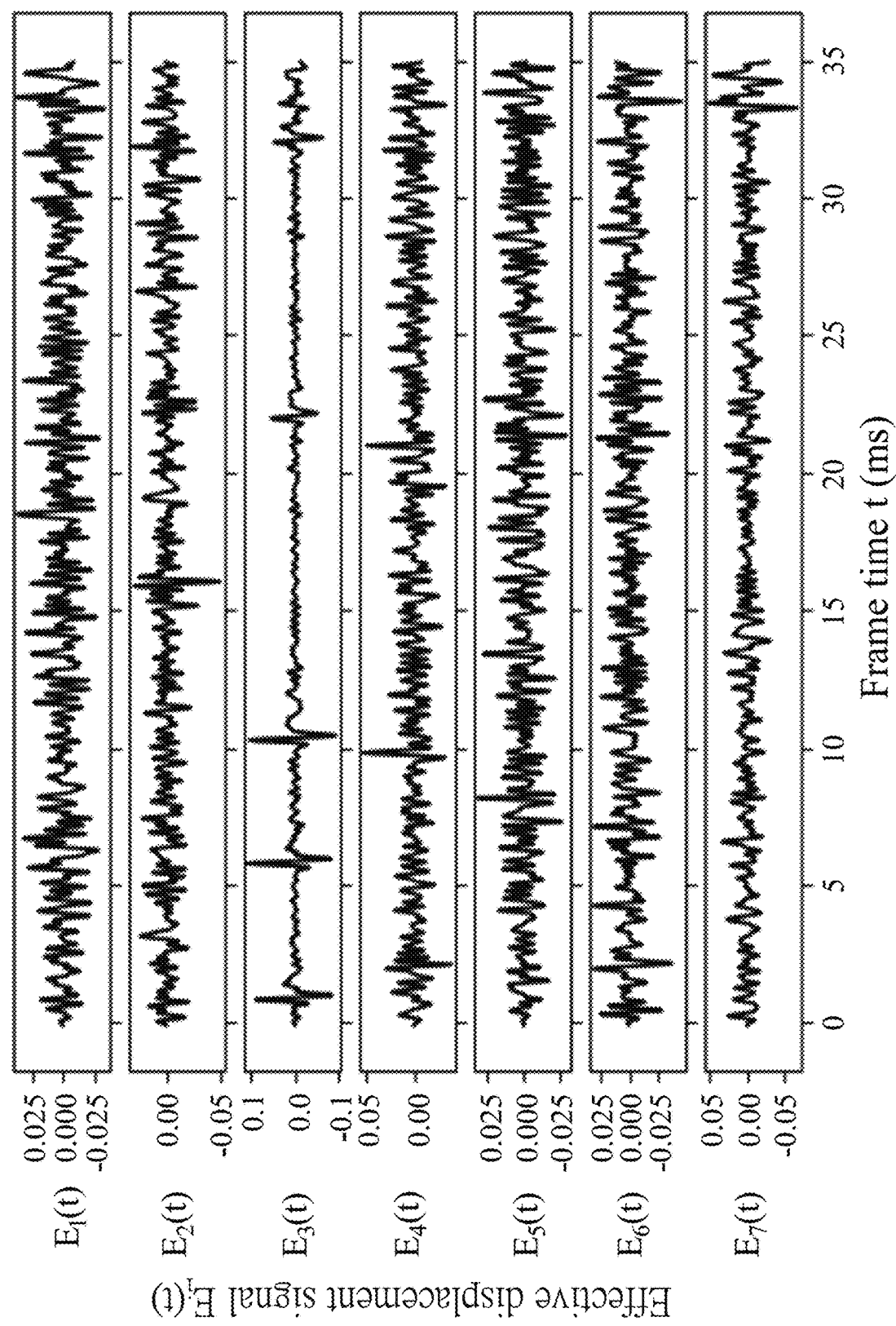
FIG. 8 is a schematic view of effective displacement signals according to the 1st embodiment.

FIG. 7 is a schematic view of original displacement signals $D_i(t)$ according to the 1st embodiment. FIG. 8 is a schematic view of effective displacement signals $E_i(t)$ according to the 1st embodiment. In FIG. 7 and FIG. 8, the effective displacement signal generating step 130 is for calculating an original displacement signal DM of each frame time t of each of the feature points (at least the feature points 991, 995, 996) from the plurality of frames of facial image data, wherein the original displacement signal $D_i(t)$ is established based on an original horizontal displacement and an original vertical displacement, and converted to an effective displacement signal $E_i(t)$. The original horizontal displacement is a displacement in a horizontal direction of each of the feature points, and the original vertical displacement is a displacement in a vertical direction of each of the feature points.

Figure 9:
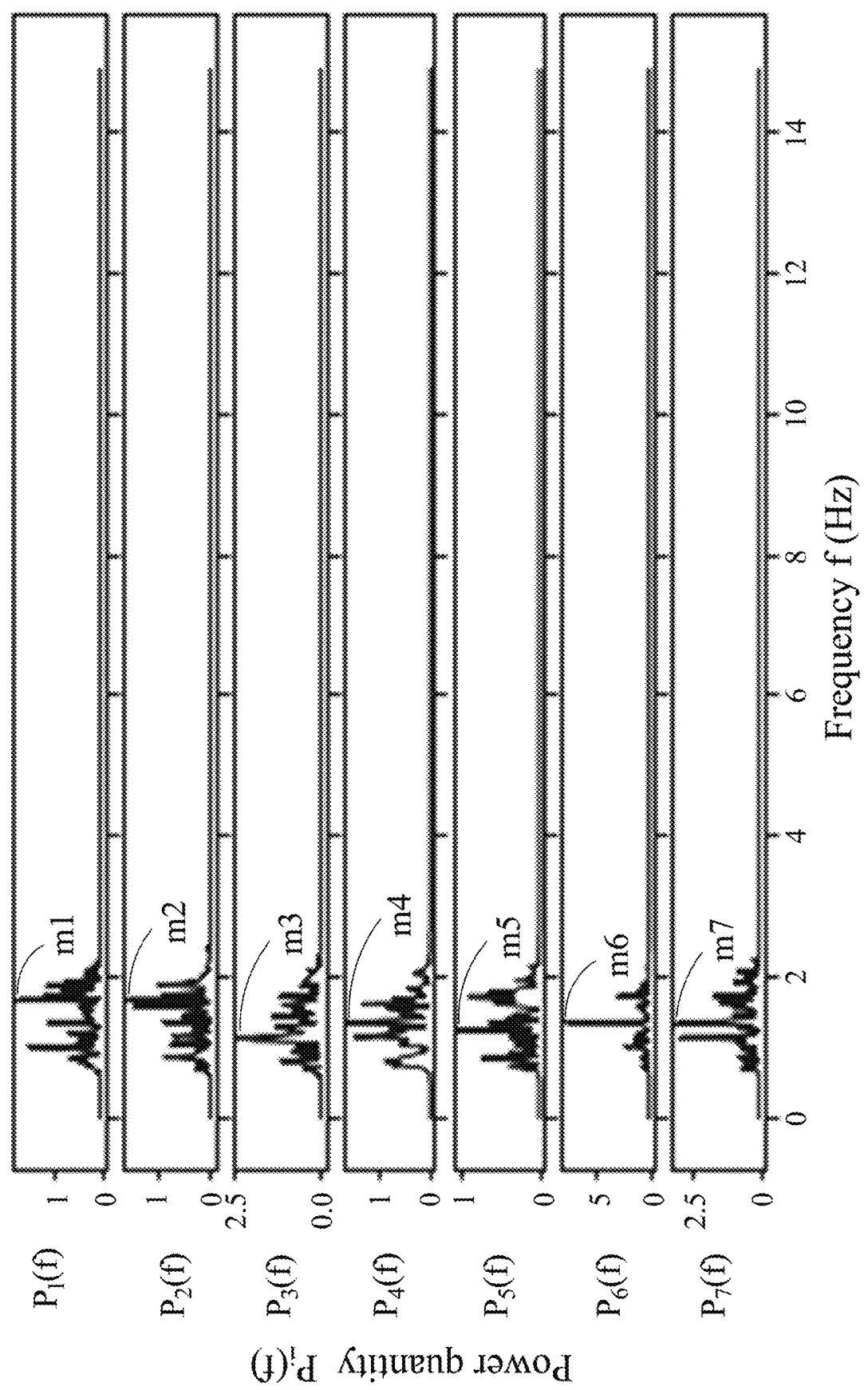
FIG. 9 is a schematic view of effective spectrums according to the 1st embodiment.

FIG. 9 is a schematic view of effective spectrums according to the 1st embodiment. In FIG. 9, the heart rate determining step 140 is for transforming the effective displacement signals $E_i(t)$ of each of the feature points (at least the feature points 991, 995, 996) to an effective spectrum, and a heart rate is determined from one of the effective spectrums corresponding to the feature points (at least the feature points 991, 995, 996), respectively. Therefore, periodic motions on the head are caused by the blood flow from the heart to the head, and the heart rate detection method 100 according to the present disclosure is related to a non-contact heart rate detection method from the face based on the aforementioned subtle motions. Moreover, the original horizontal displacements of the face are related to the dynamic balances (such as expressions, e.g. blinks), and the original vertical displacements of the face are related to the static balances, wherein the static balances are also the non-autonomous movements of the human body, including the heart rate. In the heart rate detection method 100, the original horizontal displacements and the original vertical displacements are separately considered, and the feature points 991, 995 and 996 (the center point between two medial canthi, the point of the pronasale and the point of the subnasale of the face 900, respectively), which are interfered less by the original horizontal displacements, are chosen and recognized. It is advantageous in not only simplifying the numbers of the feature points, but also avoiding mistaking an interference signal and reducing the measurement errors of the heart rate, which are resulted from too numerous feature points without a common motion mechanism but being processed by the same manners, e.g. weighting, filtering and so on.

In FIG. 2, in the feature points recognizing step 120, a plurality of landmark points 980 of the face 900 may be recognized from the plurality of frames of facial image data by an algorithm of ensemble of regression tree (ERT). A number range of the landmark points 980 is from forty to ninety, and the feature points (at least the feature points 991, 995, 996) being pre-determined of the face 900 are recognized from the landmark points 980. Therefore, it is beneficial for a proper ratio between a number of the landmark points and a number of the feature points so as to increase the efficiency and the accuracy of the feature points recognition. In the 1st embodiment, a number of the landmark points 980 is 68, and positions of the landmark points 980 are shown in FIG. 2 specifically. In addition, in the feature points recognizing step 120, the landmark points 980 of the face 900 may be recognized from the plurality of frames of facial image data further by an algorithm of histogram of gradient and an algorithm of support vector machine.

In FIG. 3 to FIG. 6, in the feature points recognizing step 120, the number range of the feature points may be from seven to twenty. That is, at least the feature points 991, 992, 993, 994, 995, 996, 997 of the face 900 are included, wherein the feature point 991 is the center point between two medial canthi, the feature point 992 is a center point between two lateral canthi, the feature point 993 is a center point of a right eye, the feature point 994 is a point of a sellion, the feature point 995 is the point of the pronasale, the feature point 996 is the point of the subnasale, and the feature point 997 is a point of a menton. Therefore, it is advantageous in reducing the errors of the heart rate detection method 100 by adding the feature points being a proper number, which are the feature points 992, 993, 994, 997, also interfered less by the original horizontal displacements. Preferably, the number range of the feature points may be from seven to ten, and at least the feature points 991, 992, 993, 994, 995, 996, 997 of the face 900 are included. In the 1st embodiment, a number of the feature points is seven, and that is the feature points 991, 992, 993, 994, 995, 996, 997. In FIG. 3 to FIG. 5, each of the feature points 991, 992, 993 is calculated from corresponding two of the landmark points 980, wherein the feature point 991 (the center point between two medial canthi) is calculated from two of the landmark points 980 respectively located on two medial canthi, the feature point 992 (the center point between two lateral canthi) is calculated from two of the landmark points 980 respectively located on two lateral canthi, and the feature point 993 (the center point of the right eye) is calculated from two of the landmark points 980 respectively located on the medial canthus and the lateral canthus of the right eye. In FIG. 6, each of the 994, 995, 996, 997 is one of the landmark points 980.

In FIG. 7, in the effective displacement signal generating step 130, the original displacement signal DM of each frame time t of each of the feature points 991, 992, 993, 994, 995, 996, 997 is calculated from the plurality of frames of facial image data, wherein the original displacement signal $D_i(t)$ is established based on the original horizontal displacement and the original vertical displacement. Specifically, in the following Equation (1), the original displacement signal $D_i(t)$ is established based on the original horizontal displacement and the original vertical displacement in the 1st embodiment, wherein $D_i(t)$ is the original displacement signal of each frame time t of one of the feature points 991, 992, 993, 994, 995, 996, 997, $X_i(t)$ is a horizontal position of each frame time t of one of the feature points 991, 992, 993, 994, 995, 996, 997, and $Y_i(t)$ is a vertical position of each frame time t of one of the feature points 991, 992, 993, 994, 995, 996, 997. Furthermore, $X_i(t)-X_i(t-1)$ is the original horizontal displacement of each frame time t of one of the feature points 991, 992, 993, 994, 995, 996, 997, and $Y_i(t)-Y_i(t-1)$ is the original vertical displacement of each frame time t of one of the feature points 991, 992, 993, 994, 995, 996, 997.

$$D_i(t)=\sqrt{[X_i(t)-X_i(t-1)]^2+[Y_i(t-1)]^2}, i=1,2,\ldots 7 \quad \text{Equation(1)}$$

The schematic views of the original displacement signals $D_1(t)$, $D_2(t)$, $D_3(t)$, $D_4(t)$, $D_5(t)$, $D_6(t)$, $D_7(t)$ according to Equation (1) of the feature points 991, 992, 993, 994, 995, 996, 997, respectively, in the 1st embodiment are shown in FIG. 7 in order from an up side to a down side. In FIG. 7, the horizontal axis represents the frame time t with the unit of ms (millisecond), and the vertical axis represents the original displacement signal $D_i(t)$. It shall be realized that the values of all the original displacement signals $D_i(t)$ can be equally scaled as needed.

Furthermore, the original displacement signal $D_i(t)$ may be calculated and converted to the effective displacement signal $E_i(t)$ by a weight of the original horizontal displacement ($X_i(t)-X_i(t-1)$ in Equation (1)) and a weight of the original vertical displacement ($Y_i(t)-Y_i(t-1)$ in Equation (1)), and the weight of the original horizontal displacement is smaller than the weight of the original vertical displacement. Therefore, it corresponds to the motion mechanism of the feature points 991, 992, 993, 994, 995, 996, 997 being pre-determined so as to reduce the interference signal related to the original horizontal displacement.

In the effective displacement signal generating step 130, the original displacement signal $D_i(t)$ may be calculated and converted to the effective displacement signal $E_i(t)$ by a fixed-point algorithm of a fast independent component analysis (FastICA) and a bandpass filter. Therefore, it is beneficial to increase the accuracy of the heart rate detection method 100. Specifically, a frequency range of a pass band of the bandpass filter is 0.75 Hz to 2 Hz, which is corresponding to 45 to 120 beats per minute of the heart rate of the human being, and the bandpass filter is a Butterworth filter. Furthermore, the weight of the original horizontal displacement and the weight of the original vertical displacement may be pre-determined constants, wherein the mathematical forms may be the original horizontal displacement to the power of at least one multiplied by the corresponding weight, the original vertical displacement to the power of at least one multiplied by the corresponding weight, the logarithm of the original horizontal displacement multiplied by the corresponding weight, the logarithm of the original vertical displacement multiplied by the corresponding weight, or others, but not limited thereto, and the weight of the original horizontal displacement is smaller than the weight of the original vertical displacement. Besides, the weight of the original horizontal displacement and the weight of the original vertical displacement may not be pre-determined constants, wherein the weight of the original horizontal displacement and the weight of the original vertical displacement may be timely adjusted according to a difference, or a ratio (but not limited thereto) between the original horizontal-displacement and the original vertical displacement of each frame time, or the calculation process equivalent to the weight of the original horizontal displacement and the weight of the original vertical displacement may be performed in the fixed-point algorithm of the fast independent component analysis.

The schematic views of the effective displacement signals $E_1(t)$, $E_2(t)$, $E_3(t)$, $E_4(t)$, $E_5(t)$, $E_6(t)$, $E_7(t)$ of the feature points 991, 992, 993, 994, 995, 996, 997, respectively, in the 1st embodiment are shown in FIG. 8 in order from an up side to a down side. In FIG. 8, the horizontal axis represents the frame time t with the unit of ms (millisecond), and the vertical axis represents the effective displacement signal $E_i(t)$. It shall be realized that the values of all the effective displacement signals $E_i(t)$ can be equally scaled as needed. Furthermore, each of the effective displacement signals $E_i(t)$ (shown in FIG. 8) in the 1st embodiment is calculated via the weight of the original horizontal displacement, the weight of the original vertical displacement, the fixed-point algorithm of the fast independent component analysis and the bandpass filter from the original displacement signals $D_i(t)$ (shown in FIG. 7). In other embodiments according to the present disclosure (not shown in drawings), each of effective displacement signals may be calculated via at least one of a weight of an original horizontal displacement, a weight of an original vertical displacement, a fixed-point algorithm of a fast independent component analysis and a bandpass filter from original displacement signals.

In FIG. 9, in the heart rate determining step 140, each of the effective displacement signals $E_1(t)$, $E_2(t)$, $E_3(t)$, $E_4(t)$, $E_5(t)$, $E_6(t)$, $E_7(t)$ of the feature points 991, 992, 993, 994, 995, 996, 997, respectively, may be transformed to the effective spectrum by a fast Fourier transform (FFT), and there is a maximum relative power in each of the effective spectrums corresponding to the feature points 991, 992, 993, 994, 995, 996, 997, respectively. The heart rate is a frequency corresponding to a maximum among the plurality of maximum relative powers corresponding to the feature points 991, 992, 993, 994, 995, 996, 997, respectively. Therefore, due to the power comparison is performed only in each single spectrum of the effective spectrums of the feature points 991, 992, 993, 994, 995, 996, 997, respectively, in the heart rate detection method 100 according to the present disclosure, it is advantageous in avoiding the power comparisons among the feature points 991, 992, 993, 994, 995, 996, 997 with different (or not completely the same) motion mechanism so as to increase the accuracy of the heart rate detection method 100.

Specifically, the schematic views of the effective spectrums of the feature points 991, 992, 993, 994, 995, 996, 997, respectively, in the 1st embodiment are shown in FIG. 9 in order from an up side to a down side, wherein the horizontal axis represents the frequency f with the unit of Hz, and the vertical axis represents power quantity $P_i(f)$ of the effective spectrum calculated from each of the effective displacement signals $E_1(t)$, $E_2(t)$, $E_3(t)$, $E_4(t)$, $E_5(t)$, $E_6(t)$, $E_7(t)$ of the feature points 991, 992, 993, 994, 995, 996, 997, respectively. The power quantities $P_1(f)$, $P_2(f)$, $P_3(f)$, $P_4(f)$, $P_5(f)$, $P_6(f)$, $P_7(f)$ are specifically shown in FIG. 9 in order from the up side to the down side, and it shall be realized that the values of all the power quantities $P_i(f)$ can be equally scaled as needed.

In the following Equation (2) and Equation (3), each of the effective spectrums of the feature points 991, 992, 993, 994, 995, 996, 997, respectively, has a maximum power $P_{i,max}$ (corresponding to a frequency $f_i$) and an average power $P_{i,avg}$, and each of the effective spectrums of the feature points 991, 992, 993, 994, 995, 996, 997, respectively, has the maximum relative power $P_{i,max}-P_{i,avg}$ (also corresponding to the frequency $f_i$). That is, the effective spectrum of the feature point 991 has the maximum power $P_{1,max}$ (corresponding to the frequency $f_1$), the average power $P_{1,avg}$ and the maximum relative power $P_{1,max}-P_{1,avg}$ (also corresponding to the frequency $f_1$); the effective spectrum of the feature point 992 has the maximum power $P_{2,max}$ (corresponding to the frequency $f_2$), the average power $P_{2,avg}$ and the maximum relative power $P_{2,max}-P_{2,avg}$ (also corresponding to the frequency $f_2$); . . . and the effective spectrum of the feature point 997 has the maximum power $P_{7,max}$ (corresponding to the frequency $f_7$), the average power $P_{7,avg}$ and the maximum relative power $P_{7,max}-P_{7,avg}$ (also corresponding to the frequency $f_7$).

$$P_{i,max} = \max(P_i(f)), i=1,2,\ldots 7 \quad \text{Equation (2)}$$

$$P_{i,avg} = \text{avg}(P_i(f)), i=1,2,\ldots 7 \quad \text{Equation (3)}$$

In FIG. 9, the effective spectrums of the feature points 991, 992, 993, 994, 995, 996, 997 respectively have maximum power points m1, m2, m3, m4, m5, m6, m7, which are respectively corresponding to the maximum powers $P_{1,max}$, $P_{2,max}$, $P_{3,max}$, $P_{4,max}$, $P_{5,max}$, $P_{6,max}$, $P_{7,max}$ in the vertical axis, and respectively corresponding to the frequencies $f_1$, $f_2$, $f_3$, $f_4$, $f_5$, $f_6$, $f_7$ in the horizontal axis. Furthermore, it can be realized that the effective spectrums of the feature points 991, 992, 993, 994, 995, 996, 997 respectively have the maximum relative powers $P_{1,max}-P_{1,avg}$, $P_{2,max}-P_{2,avg}$, $P_{3,max}-P_{3,avg}$, $P_{4,max}-P_{4,avg}$, $P_{5,max}-P_{5,avg}$, $P_{6,max}-P_{6,avg}$, $P_{7,max}-P_{7,avg}$, which are also respectively corresponding to the frequencies f1, f2, f3, f4, f5, f6, f7.

Moreover, in the following Equation (4) to Equation (6), $P_{\alpha,max}-P_{\alpha,avg}$ (i.e. $i=\alpha$ in Equation (4)) is the maximum among the plurality of maximum relative powers $P_{1,max}-P_{1,avg}$, $P_{2,max}-P_{2,avg}$, $P_{3,max}-P_{3,avg}$, $P_{4,max}-P_{4,avg}$, $P_{5,max}-P_{5,avg}$, $P_{6,max}-P_{6,avg}$, $P_{7,max}-P_{7,avg}$. The frequency $f_\alpha$ corresponding to the maximum relative power $P_{\alpha,max}-P_{\alpha,avg}$ (the frequency $f_\alpha$ also corresponding to the maximum power $P_{\alpha,max}$) is the heart rate, which is denoted as Index in Equation (5)) with the unit of Hz. The heart rate may be further calculated via a unit conversion. That is, the frequency $f_\alpha$ corresponding to the maximum relative power $P_{\alpha,max}-P_{\alpha,avg}$ (the frequency $f_\alpha$ also corresponding to the maximum power $P_{\alpha,max}$) is the Index according to Equation (5), and then the heart rate HR with the unit of 1/minute is calculated via the unit conversion according to Equation (6).

$$\alpha = \arg_i \max(P_{i,max}-P_{i,avg}), i=1,2,\ldots 7 \quad \text{Equation (4)}$$

$$\text{Index} = \arg_f \max(P_\alpha(f)) \quad \text{Equation (5)}$$

$$HR = 60 \times \text{Index} \quad \text{Equation (6)}$$

For example as FIG. 9, the effective spectrums of the feature points 991, 992, 993, 994, 995, 996, 997 respectively have the maximum power points m1, m2, m3, m4, m5, m6, m7, which are respectively corresponding to the maximum relative powers $P_{1,max}-P_{1,avg}$, $P_{2,max}-P_{2,avg}$, $P_{3,max}-P_{3,avg}$, $P_{4,max}-P_{4,avg}$, $P_{5,max}-P_{5,avg}$, $P_{6,max}-P_{6,avg}$, $P_{7,max}-P_{7,avg}$, wherein the maximum thereamong is the maximum relative power $P_{6,max}-P_{6,avg}$ of the maximum power point m6 of the feature point 996 (i.e. the point of the subnasale of the face 900). The frequency $f_6$ corresponding to the maximum power point m6 is the heart rate (Index) with the unit of Hz, and the heart rate HR with the unit of 1/minute can be conversed via the unit conversion.

Figure 10:
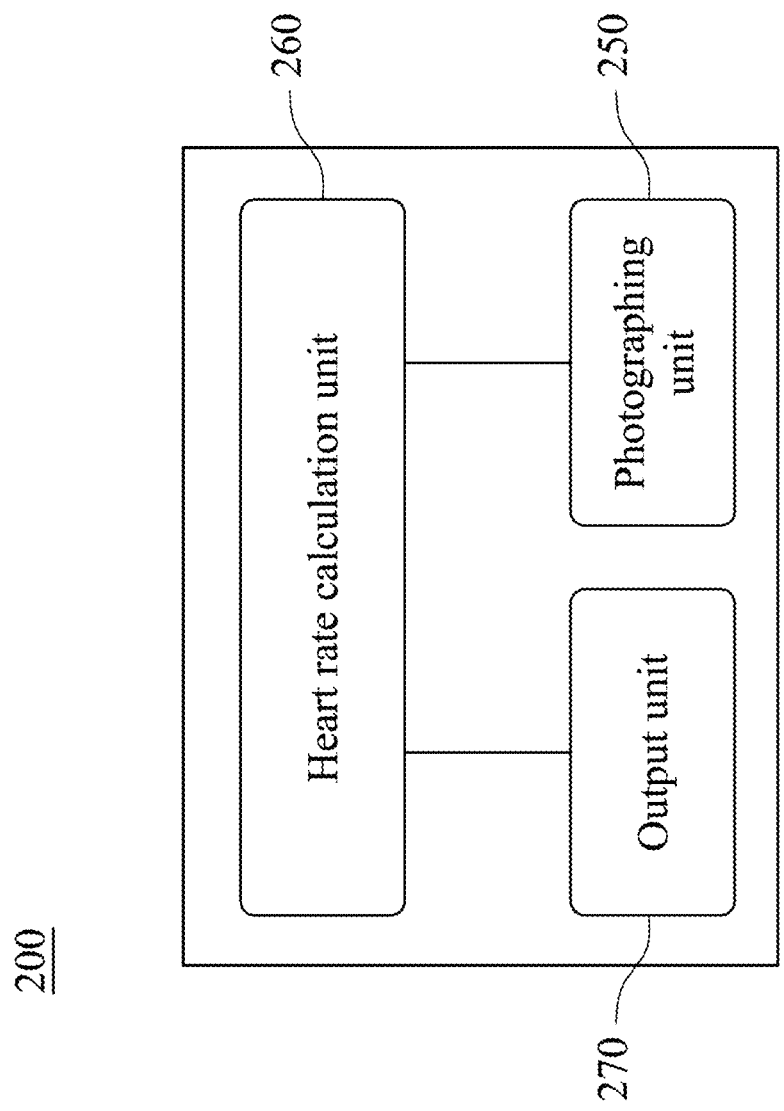
FIG. 10 is a block diagram of a heart rate detection device according to the 2nd embodiment of the present disclosure.

FIG. 10 is a block diagram of a heart rate detection device 200 according to the 2nd embodiment of the present disclosure. In FIG. 10, the heart rate detection device 200 includes a photographing unit 250, a heart rate calculation unit 260 and an output unit 270.

Please refer to the aforementioned paragraphs of the heart rate detection method 100 of the 1st embodiment together. In the 2nd embodiment, the photographing unit 250 is configured to provide the plurality of frames of facial image data of the face 900. The heart rate calculation unit 260 is communicatively connected to the photographing unit 250, wherein the heart rate calculation unit 260 is configured to recognize the plurality of feature points, which are predetermined, of the face 900 from the plurality of frames of facial image data, and the number range of the feature points is from three to twenty. That is, at least the feature points 991, 995, 996 of the face 900 are included, wherein the feature point 991 is the center point between two medial canthi of the face 900, the feature point 995 is the point of the pronasale of the face 900, and the feature point 996 is the point of the subnasale of the face 900. The effective displacement signal $E_i(t)$ of each frame time t of each of the feature points (at least the feature points 991, 995, 996) is calculated from the plurality of frames of facial image data, the effective displacement signals $E_i(t)$ of each of the feature points (at least the feature points 991, 995, 996) are transformed to the effective spectrum, and the heart rate is determined from one of the effective spectrums corresponding to the feature points (at least the feature points 991, 995, 996), respectively. The output unit 270 is communicatively connected to the heart rate calculation unit 260, wherein the heart rate is outputted to the output unit 270 from the heart rate calculation unit 260. Therefore, it is advantageous in avoiding mistaking an interference signal and reducing the measurement errors of the heart rate so as to increase the accuracy of the heart rate detection device 200. In addition, the output unit 270 may be at least one of a storage apparatus, a display and a speaker, but not limited thereto.

In detail, the number range of the feature points may be from seven to twenty. That is, at least the feature points 991, 992, 993, 994, 995, 996, 997 of the face 900 are included, wherein the feature point 991 is the center point between two medial canthi, the feature point 992 is the center point between two lateral canthi, the feature point 993 is the center point of the right eye, the feature point 994 is the point of the sellion, the feature point 995 is the point of the pronasale, the feature point 996 is the point of the subnasale, and the feature point 997 is the point of the menton. Therefore, it is advantageous in reducing the errors of the heart rate detection device 200 by adding the feature points being a proper number, which are feature points 992, 993, 994, 997, also interfered less by the original horizontal displacements.

Furthermore, the heart rate calculation unit 260 may be configured to generate the original displacement signal $D_i(t)$ of each frame time of each of the feature points 991, 992, 993, 994, 995, 996, 997 calculated from the plurality of frames of facial image data. The original displacement signal $D_i(t)$ is calculated and converted to the effective displacement signal $E_i(t)$ by the weight of the original horizontal displacement (i.e. $X_i(t)-X_i(t-1)$ in Equation (1)) and the weight of the original vertical displacement (i.e. $Y_i(t)-Y_i(t-1)$ in Equation (1)). The weight of the original horizontal displacement is smaller than the weight of the original vertical displacement, Therefore, it corresponds to the motion mechanism of the feature points 991, 992, 993,

994, 995, 996, 997 being pre-determined so as to reduce the interference signal related to the original horizontal displacement.

The effective displacement signals $E_i(t)$ of each of the feature points 991, 992, 993, 994, 995, 996, 997 may be transformed to the effective spectrum by the Fourier transform, there is the maximum relative power (i.e. $P_{i,max}-P_{i,avg}$ in Equation (4)) in each of the effective spectrums corresponding to the feature points 991, 992, 993, 994, 995, 996, 997, respectively, and the heart rate is the frequency corresponding to the maximum among the plurality of maximum relative powers. Therefore, due to the power comparison is performed only in each single spectrum of the effective spectrums of the feature points 991, 992, 993, 994, 995, 996, 997, respectively, in the heart rate detection device 200 according to the present disclosure, it is advantageous in avoiding the power comparisons among the feature points 991, 992, 993, 994, 995, 996, 997 with different (or not completely the same) motion mechanism so as to increase the accuracy of the heart rate detection device 200.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A heart rate detection method, comprising:
   a facial image data acquiring step for acquiring a plurality of frames of facial image data of a face;
   a feature points recognizing step for recognizing a plurality of feature points, which are pre-determined, of the face from the plurality of frames of facial image data, wherein a number range of the feature points is from three to twenty, and the feature points comprise a center point between two medial canthi, a point of a pronasale and a point of a subnasale of the face;
   an effective displacement signal generating step for calculating an original displacement signal of each frame time of each of the feature points from the plurality of frames of facial image data, wherein the original displacement signal is established based on an original horizontal displacement and an original vertical displacement, and converted to an effective displacement signal; and
   a heart rate determining step for transforming the effective displacement signals of each of the feature points to an effective spectrum, wherein a heart rate is determined from one of the effective spectrums corresponding to the feature points, respectively.

2. The heart rate detection method of claim 1, wherein, in the feature points recognizing step, a plurality of landmark points of the face are recognized from the plurality of frames of facial image data by an algorithm of ensemble of regression tree, a number range of the landmark points is from forty to ninety, and the feature points being pre-determined of the face are recognized from the landmark points.

3. The heart rate detection method of claim 1, wherein the number range of the feature points is from seven to twenty, and the feature points further comprise a center point between two lateral canthi, a center point of a right eye, a point of a sellion and a point of a menton of the face.

4. The heart rate detection method of claim 1, wherein, in the effective displacement signal generating step, each of the original displacement signals is calculated and converted to the effective displacement signal by a weight of the original horizontal displacement and a weight of the original vertical displacement, and the weight of the original horizontal displacement is smaller than the weight of the original vertical displacement.

5. The heart rate detection method of claim 1, wherein, in the effective displacement signal generating step, each of the original displacement signals is calculated and converted to the effective displacement signal by a fixed-point algorithm of a fast independent component analysis and a bandpass filter.

6. The heart rate detection method of claim 1, wherein, in the heart rate determining step, the effective displacement signals of each of the feature points are transformed to the effective spectrum by a Fourier transform, there is a maximum relative power in each of the effective spectrums corresponding to the feature points, respectively, and the heart rate is a frequency corresponding to a maximum among the plurality of maximum relative powers.

7. A heart rate detection device, comprising:
   a photographing unit configured to provide a plurality of frames of facial image data of a face;
   a heart rate calculation unit communicatively connected to the photographing unit, wherein the heart rate calculation unit is configured to recognize a plurality of feature points, which are pre-determined, of the face from the plurality of frames of facial image data, a number range of the feature points is from three to twenty, the feature points comprise a center point between two medial canthi, a point of a pronasale and a point of a subnasale of the face, an effective displacement signal of each frame time of each of the feature points is calculated from the plurality of frames of facial image data, the effective displacement signals of each of the feature points are transformed to an effective spectrum, and a heart rate is determined from one of the effective spectrums corresponding to the feature points, respectively; and
   an output unit communicatively connected to the heart rate calculation unit, wherein the heart rate is outputted to the output unit from the heart rate calculation unit.

8. The heart rate detection device of claim 7, wherein the number range of the feature points is from seven to twenty, and the feature points further comprise a center point between two lateral canthi, a center point of a right eye, a point of a sellion and a point of a menton of the face.

9. The heart rate detection device of claim 7, wherein the heart rate calculation unit is configured to generate an original displacement signal of each frame time of each of the feature points calculated from the plurality of frames of facial image data, the original displacement signal is calculated and converted to the effective displacement signal by a weight of an original horizontal displacement and a weight of an original vertical displacement, and the weight of the original horizontal displacement is smaller than the weight of the original vertical displacement.

10. The heart rate detection device of claim 7, wherein the effective displacement signals of each of the feature points are transformed to the effective spectrum by a Fourier transform, there is a maximum relative power in each of the effective spectrums corresponding to the feature points, respectively, and the heart rate is a frequency corresponding to a maximum among the plurality of maximum relative powers.

\* \* \* \* \*